United States Patent
Kaiser

(10) Patent No.: US 7,230,430 B1
(45) Date of Patent: Jun. 12, 2007

(54) FAST MICROCALORIMETRY FOR ELECTROCHEMICAL CELLS

(75) Inventor: Donald F. Kaiser, Clarence Center, NY (US)

(73) Assignee: Greatbatch, Inc., Clarence, NY (US)

( * ) Notice: Subject to any disclaimer, the term of this patent is extended or adjusted under 35 U.S.C. 154(b) by 0 days.

(21) Appl. No.: 11/164,548

(22) Filed: Nov. 29, 2005

Related U.S. Application Data

(60) Provisional application No. 60/631,831, filed on Nov. 30, 2004.

(51) Int. Cl.
*G01R 31/36* (2006.01)
*G01N 25/20* (2006.01)
*G01N 25/18* (2006.01)

(52) U.S. Cl. ............. 324/441; 324/426; 324/432; 374/44

(58) Field of Classification Search .......... 324/441, 324/426; 374/44
See application file for complete search history.

(56) References Cited

U.S. PATENT DOCUMENTS

| | | | | |
|---|---|---|---|---|
| 3,931,573 A | * | 1/1976 | Hopfer | 324/106 |
| 4,999,576 A | * | 3/1991 | Levinson | 324/142 |
| 5,315,228 A | | 5/1994 | Hess et al. | |
| 5,964,903 A | * | 10/1999 | Gao et al. | 29/623.1 |
| 6,215,281 B1 | | 4/2001 | Koch | |
| 6,225,780 B1 | | 5/2001 | Koch | |
| 6,492,831 B2 | | 12/2002 | Hashimoto | |
| 6,522,103 B1 | * | 2/2003 | Miyoshi et al. | 320/136 |
| 6,636,751 B1 | * | 10/2003 | McCartney | 455/572 |
| 6,661,203 B2 | * | 12/2003 | Wolin et al. | 320/134 |
| 6,825,669 B2 | * | 11/2004 | Raichle et al. | 324/426 |
| 6,919,725 B2 | * | 7/2005 | Bertness et al. | 324/433 |
| 6,928,381 B2 | * | 8/2005 | Becker-Irvin et al. | 702/130 |
| 2004/0257089 A1 | * | 12/2004 | Aridome | 324/430 |
| 2005/0077615 A1 | * | 4/2005 | Yu et al. | 257/706 |

* cited by examiner

*Primary Examiner*—Walter Benson
*Assistant Examiner*—John Zhu
(74) *Attorney, Agent, or Firm*—Michael F. Scalise

(57) ABSTRACT

The present invention broadly comprises a method and apparatus for testing electrochemical cells which is faster and more cost-effective than current testing methods. Accordingly, the invention provides a method for testing electrochemical cells, particularly batteries for medical applications, such as for implantable devices for pacemakers, defibrillators, etc., comprising the steps of: surrounding at least one electrochemical cell with a vacuum with a pressure range of 0 to 0.001 Torr and measuring energy emitted from the electrochemical cell.

26 Claims, 2 Drawing Sheets

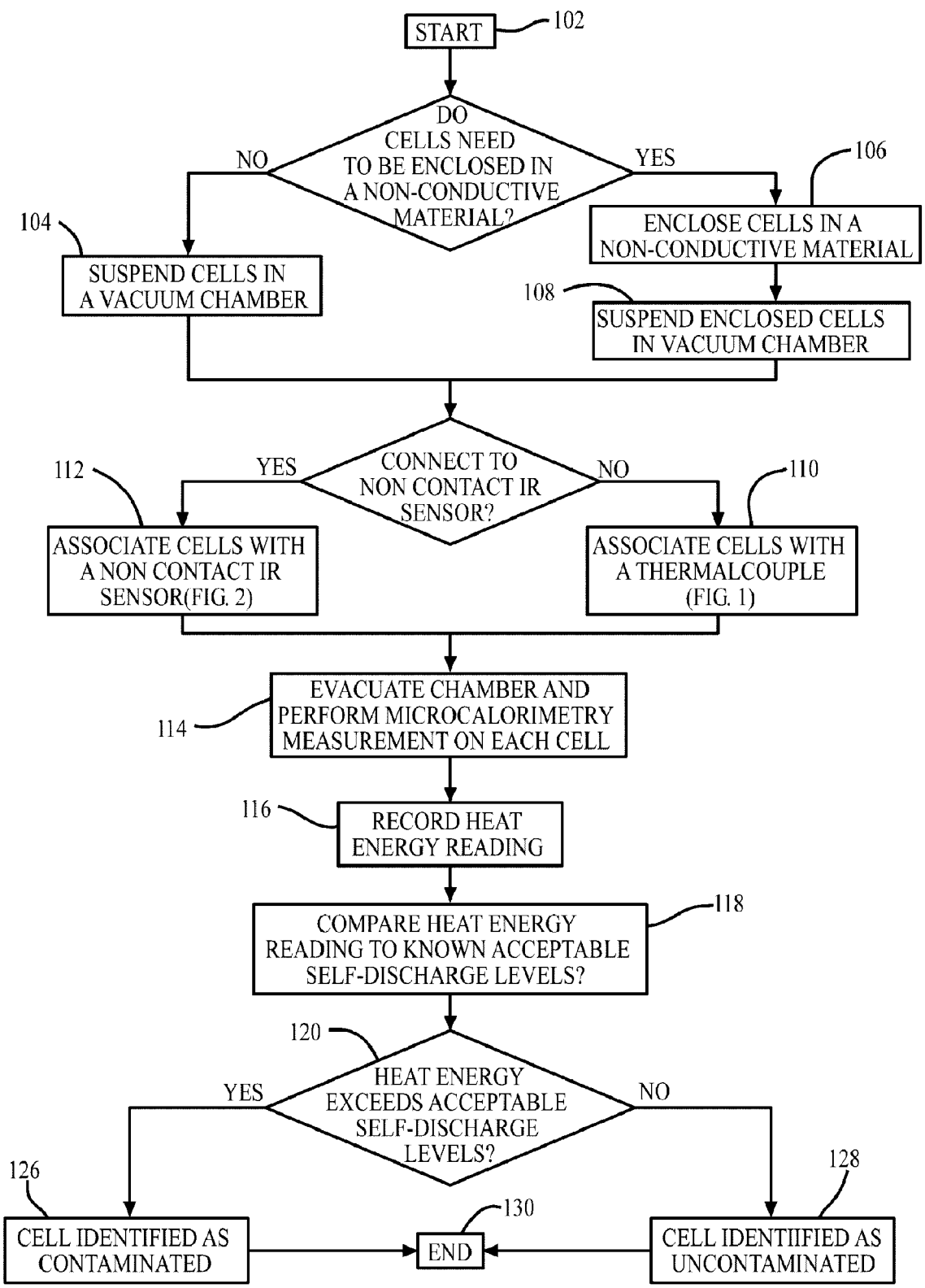

FAST MICROCALORIMETRY FOR ELECTROCHEMICAL CELLS

DESCRIPTION

Field of the Invention

This invention relates generally to a device and method for performing microcalorimetry measurements on electrochemical cells, in particular batteries, in a shortened period of time. In particular, microcalorimetry measurements are performed in insulated or low pressure environments.

BACKGROUND OF THE INVENTION

Minute quantities of contaminant in an electrochemical cell, such as a battery, can lead to premature failure of the cell. In many cases, contamination elevates the rate of self-discharge within the cell. This self-discharge produces relatively low levels of heat energy within the cell, typically on the order of 10-100 microwatts for an implantable medical type battery. Microcalorimetry techniques can be used to measure this heat energy, quantify the self-discharge rate, and identify a potentially contaminated cell.

Microcalorimetry instrumentation for measuring the low energy levels referenced above, is presently commercially available. Notwithstanding, the time required to perform a microcalorimetry measurement is typically 2 to 4 hours for a single cell. The extraordinarily long period needed to test a single cell is due to the difficulty in measuring the low energy levels associated with a faulty cell. Sensing low energy output against an ambient environment can only be done over a long period of time with conventional insulating and testing techniques. Consequently, conventional microcalorimetry techniques for screening cells have been prohibitively slow and expensive for use in production settings.

Reducing the time needed for testing electrochemical cells is complicated by the difficulty in differentiating low energy levels emitted from self-discharging cells from ambient environments. Thermocouples are incapable of measuring low energy levels in an ambient environment that masks self-discharging energy emissions.

While it is an option to thermally insulate electrochemical cells in a typical production environment, it is only viable if the temperature rise is relatively large, on the order of one degree Celsius or more. To achieve this for a cell with a surface area on the order of 10 $cm^2$, which is roughly the surface area for a typical implantable medical battery, would require a thermal insulation R-factor on the order of 60 or greater. Even the best of modern insulation materials cannot provide this level of insulation for a specimen with such a small surface area.

Accordingly, there is a need for a microcalorimetry technique and system that would enable measurement of low level energy associated with self-discharge from electrochemical cells, such as implantable medical cells in a shortened period of time.

SUMMARY OF THE INVENTION

It is a principal object of the invention to provide a method for testing electrochemical cells which is faster and more cost-effective than current testing methods. Accordingly, one principal object of the invention is to provide a method for testing electrochemical cells, particularly batteries for medical applications, such as for implantable pacemakers, defibrillators, etc., comprising the steps of: surrounding at least one electrochemical cell with a vacuum and measuring energy emitted from the electrochemical cell. In yet an alternative aspect of the invention a method is provided for placement of the electrochemical cell in a vacuum chamber. The methods of the invention provide for measuring energy output of a battery using a thermocouple or a non-contact heat sensing device. The non-contact heat sensing device may be a non-contact IR heat sensing device. Alternatively, the non-contact IR heat sensing device may be movable relative to the battery. The vacuum is preferably in a range of 0 to 0.001 Torr.

The methods of the invention also contemplate surrounding the electrochemical cell, e.g., battery, with a thermal insulation R-factor in the range 60-250. The electrochemical cell may be hermetically sealed or it can be air permeable, wherein the method includes the step of surrounding the electrochemical cell with a hermetically sealed enclosure employing known techniques. Alternatively, when the electrochemical cell is defective, measuring energy discharge further comprises measuring a first heat energy. Then, the method compares the first heat energy to a second heat energy associated with a standardized electrochemical cell, and in response thereto identifies the defect in the cell being tested.

The present invention generally comprises a system for testing an electrochemical cell. The testing system comprises a chamber configured to reduce a pressure therein; at least one heat energy measuring device disposed within the chamber and configured to measure heat energy associated with an electrochemical cell, such as a battery disposed in the chamber; and at least one support to suspend the electrochemical cell.

These and other objects, features, and advantages of the present invention will become more readily apparent to those having ordinary skill in the art upon reading the following detailed description of the invention in view of the drawings hereinbelow.

BRIEF DESCRIPTION OF THE DRAWINGS

The nature and mode of operation of the present invention will now be more fully described in the following detailed description of the invention taken with the accompanying drawing figures, in which:

FIG. 3 is a flow diagram illustrating the method of testing electrochemical cells as taught by the present invention.

DETAILED DESCRIPTION OF THE INVENTION

At the outset, it should be appreciated that like drawing numbers on different drawing views identify identical structural elements of the invention. While the present invention is described with respect to what is presently considered to be the preferred embodiments, it is understood that the invention is not limited to the disclosed embodiments.

Figure 1:
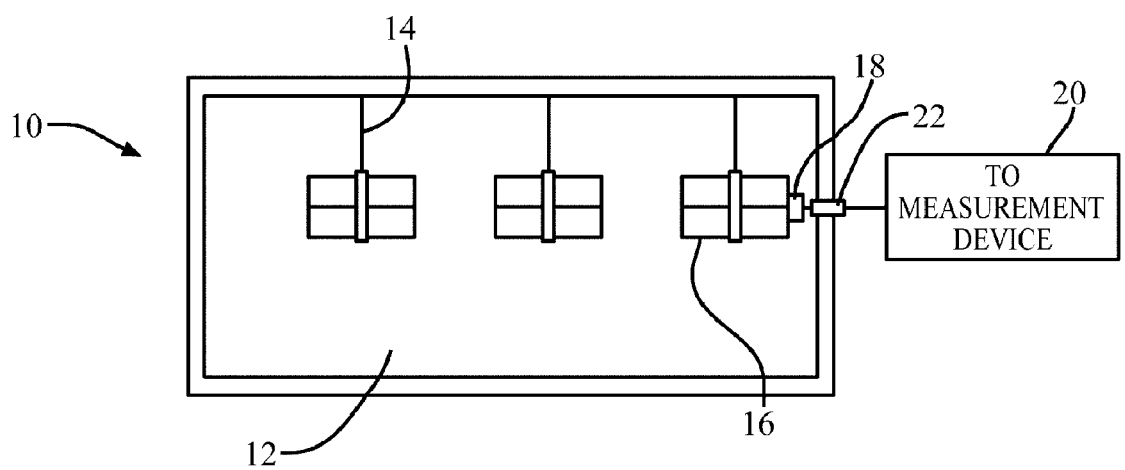
FIG. 1 is a schematic of a first embodiment of the invention depicting a system for testing electrochemical cells.

FIG. 1 is a schematic of a first embodiment of the invention for testing electrochemical cells for contamination. System 10 includes vacuum chamber 12, used to house the batteries 16 being tested under low pressure environments. In one aspect, the pressure in system 10 is reduced to <0.001 Torr. Using support elements 14, electrochemical cells 16 are suspended in chamber 12 and tested for defects. In general, cells 16 are suspended within vacuum chamber 12 out of contact with other cells being tested. Suspension apparatus 14 used in vacuum chamber 12 may be constructed of materials having greatly reduced heat conductance. A fine filament wire or thread of relatively low thermal conductivity having a high ratio of length to cross-sectional area, such as a filament, is needed. Suitable materials include glass, ceramic, and thermoplastic materials. Such materials having a spun or foamed construction with low thermal conductivities are particularly desirable.

The support apparatus 14 may comprise a sling that cradles cell 16, such as around the midsection of the cell. Preferably, support apparatus 14 is suitable for supporting electrochemical cell 16, so as to minimize or eliminate rotation of cell 16 from making contact with adjacent cells being tested.

The amount of heat energy being emitted by cells 16 in the form of temperature rise is measured. Heat energy emitted from the cells can be measured by any means known by persons skilled in the art and compatible with the conditions in chamber 12. One preferred method would be by employing thermocouple 18 used to measure heat from cells 16. One defect that can be detected using system 10 is contamination of cells 16. For example, as noted supra, contaminated cells are characterized by elevated heat energy outputs. These elevated outputs, in the range of 1 to 100 microwatts, can be quickly and accurately detected using thermocouple 18.

Output signals from the thermocouple 18 are registered on instrumentation 20, such as a voltage meter, or other similar type instrumentation known among ordinary skilled artisans in the field. Suitable circuitry relays the signal from thermocouple 18 through a hermetic feedthrough 22 in the wall of the chamber 12 to instrumentation 20, which registers and displays the temperature rise above ambient, which is indicative of heat energy emitted from cells 16. In that respect, good instrumentation practices for measuring temperature, which are well known to those skilled in the art, are necessary for measuring the heat energy temperature rise.

In vacuum chamber 12, pressures between 0 and 0.001 Torr produce a thermal insulation R-factor of 250, or greater. The resulting thermal insulation factor created by a high vacuum condition is advantageous for producing the conditions necessary for testing the heat energy emitted from an electrochemical cell over a shortened time period. Since heat energy self-discharge rates from batteries are extremely low, on the order of approximately 10-100 microwatts, placing electrochemical cells in an insulated environment according to the present invention effectively reduces the time needed to identify the heat energy self-discharge from the cell.

As it is used in this context, the term vacuum denotes an environment that is close to 0 Torr, but the insulating benefits of a high vacuum environment are recognized within a range of pressures. In this context the vacuum can include pressures within a range of 0 to about 0.001 Torr. It is preferred that pressure surrounding the electrochemical cells be 0 Torr, but if the pressure reaches 0.001 Torr the thermal insulation factor will be sufficient to perform the testing method. Between 0.01 to 0.001 Torr, the R-factor changes with increasing pressure so the vacuum pressure is needed in order to determine the R-factor. However, at about 0.001 Torr and below, the R-factor is effectively constant at about 250.

Typically, implantable medical grade batteries are hermetically sealed, so a high vacuum condition causes no detrimental effects to those devices. Therefore, batteries of these types can be placed in chamber 12 for testing without the necessity of providing ancillary protection for them.

Placing batteries that are not hermetically sealed or that are permeable to air in a vacuum can result in significant damage to the cells. However, in some aspects, non-vacuum sealed cells, or air permeable cells can be tested in chamber 12 by surrounding the cells with an outer enclosure that hermetically seals the cells. In that case, the thermocouple 18 is placed in physical contact with each hermetic enclosure housing an air permeable cell. This contact does not significantly degrade the insulation levels around the cell.

Figure 2:
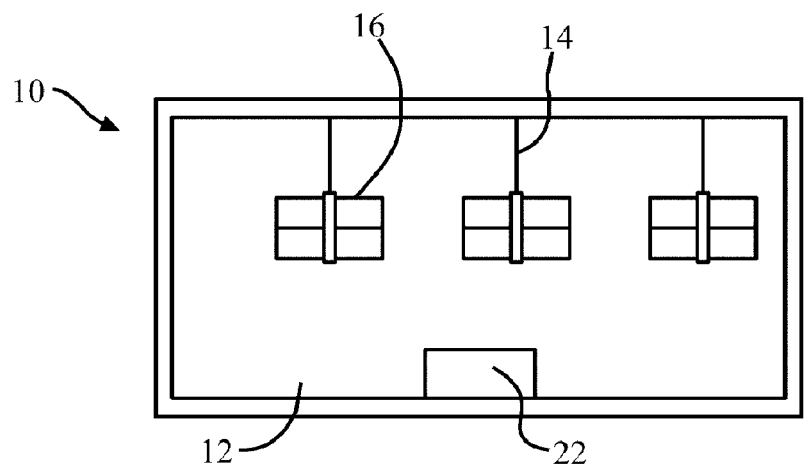
FIG. 2 is a schematic of a second embodiment of the invention for testing electrochemical cells.

FIG. 2 represents a second preferred embodiment of the invention for testing electrochemical cells, such as batteries. As noted above, any measuring means known in the art can be used in system 10. In some aspects, a non-contact temperature sensing device is used in system 10. Such devices include, but are not limited to: IR optical sensors and remote non-contact IR thermometers. In FIG. 2, IR optical sensor 22 is used.

Alternatively, a device suitable for lateral translation (not shown) of optical sensor 22 may be used to facilitate the use of a single non-contact infrared sensor with each testing chamber. That is, the non-contact infrared sensor can be repositioned and focused on each battery in the chamber in successive fashion. An actuator, such as a stepper motor (not shown) to move the infrared sensing device eliminates the need for multiple infrared sensors, resulting in a cost savings and economic benefit. Sensing heat energy in this fashion is quick and efficient. The infrared sensor is moved successfully along the chamber and positioned in front of each cell, but other configurations may be used. For example, an optical infrared sensor can be positioned in a central location and refocused on each cell to be tested, as opposed to moving the entire sensor with a stepper actuator.

Electrochemical cells that are free of defects have an acceptable self-discharge rate of heat energy. The acceptable rate for each cell model and type is known or can be determined. For example, industry standard self-discharge rates are known for many batteries and heat energy levels from cells that are tested can be compared to those standardized levels to make a determination whether a cell is contaminated. By comparing heat discharge rates measured in system 10 with standardized rates, batteries with self-discharge rates that are significantly above such rates can be identified. Based on the differences in these rates, the type of defect, for example, contamination can be identified.

It should be understood that the present invention is not limited to measuring defects associated with contamination and that the identification of other defects or characteristics of cells measured by system 10 is within the spirit and scope of the invention as claimed.

It is advantageous to test multiple electrochemical cells simultaneously. With previous microcalorimetry techniques, and using conventional insulating materials, from 2 to 4 hours are required to test a single cell. These methods of the present invention provide that the use of a vacuum chamber, which increases the insulation effect for multiple cells simultaneously, makes it possible to test multiple cells in minutes, rather than hours using conventional microcalorimetry and insulation techniques. The number of cells tested simultaneously with this method is only limited by the size of the vacuum chamber, and that a sufficient number of temperature measuring devices are provided for the respective number of cells being tested. By surrounding electrochemical cells with a vacuum, the cells are insulated from the ambient environment which allows even miniscule heat energy emissions from cells to be measured quickly.

FIG. 3 is a flow diagram illustrating the methods for testing electrochemical cells according to the present invention. Initially, electrochemical cells are suspended 104 from support apparatus 14 (shown in FIG. 1), which is preferably of relatively low thermal conductivity, within vacuum chamber 12 (shown in FIG. 1). Alternatively, cells can be enclosed within a material 106 of relatively low thermal conductivity and then placed 108 within the vacuum chamber 12.

After the cells are housed in a vacuum chamber, a thermocouple 18 (shown in FIG. 1) is placed in contact with each cell 100. In other embodiments, the method includes using a non-contact infrared sensor to detect the heat emitted from each cell 112, as described above. Next, air is evacuated from vacuum chamber 12 which leads to a decreased in pressure therein 114. Pressure is decreased to a point that creates a thermal insulating R-factor of at least 60, and preferably 250. The vacuum environment that creates this insulating effect is achieved as the pressure approaches 0 Torr. Although it is preferred that 0 Torr be achieved within vacuum chamber 12, ranges of pressure from 0 to 0.001 Torr are sufficient. Once pressure within vacuum chamber 12 reaches this range a vacuum environment has been accomplish and the cells can be tested.

Each thermocouple device or non-contact sensor is linked with instrumentation that registers the heat energy emitted for the cells being tested in the vacuum environment 114. As the microcalorimetry measurements are registered by the thermocouple or the non-contact infrared sensor, these measurements are recorded 116. The recorded heat energy readings are then compared to standardized self-discharge levels 118. A determination is made as to whether the self-discharge of heat emitted from the cell being tested exceeds standardized discharge levels for the particular model or class of electrochemical cell 120. Cells that have self-discharge heat levels that exceed standardized levels 122 for the particular model or class are identified as defective or contaminated 126. Cells that have self-discharge heat levels that are acceptable for the particular model 124 are identified as non-defective or uncontaminated 128.

Thus, it is seen that the objects of the present invention are efficiently obtained, although modifications and changes to the invention should be readily apparent to those having ordinary skill in the art, and these modifications are intended to be within the spirit and scope of the invention as claimed.

What is claimed is:

1. A method of testing an electrochemical cell, comprising the steps of:
    a) providing a chamber capable of being sealed and then evacuated to provide a vacuum therein;
    b) providing a filament having a length between first and second ends;
    c) attaching the first end of the filament to the chamber and the second end to at least one electrochemical cell, thereby hanging the cell in the vacuum by the filament; and
    d) measuring energy emitted from the at least one electrochemical cell.

2. The method of claim 1 wherein the energy measured is in the form of a temperature rise.

3. The method of claim 1 wherein the at least one electrochemical cell is hermetically sealed.

4. The method of claim 1 wherein the at least one electrochemical cell is suitable for implantable medical applications.

5. The method of claim 1 wherein the vacuum is in a range of 0 to 0.001 Torr.

6. The method of claim 1 further comprising: surrounding the at least one electrochemical cell with a thermal insulation R-factor in the range of 60 hr×ft$^2$ ×° F/BTU×in to 250 hr×ft$^2$ ×° F/BTU×in.

7. The method of claim 1 wherein the at least one electrochemical cell comprises a defect and the further steps of:
    a) measuring a first heat energy emitted from a first electrochemical cell;
    b) comparing the first heat energy to a second heat energy emitted from a defect-free electrochemical cell; and
    c) in response to the comparison, identifying whether there is a defect in the first electrochemical cell, or not.

8. The method of claim 1 wherein the at least one electrochemical cell is air permeable and the method further comprising: sealing the at least one electrochemical cell in the chamber prior to providing the vacuum therein.

9. The method of claim 1 including providing the filament as a fine wire or thread of relatively low thermal conductivity and a relatively high ratio of length to cross-sectional area.

10. The method of claim 1 including selecting the filament from the group consisting of glass, ceramics, and thermoplastic materials.

11. The method of claim 1 including providing the filament of a spun or foamed construction.

12. A system for testing an electrochemical cell for defects, comprising:
    a) a sealable chamber capable of having a vacuum provided therein;
    b) a filament having a length between first and second ends, wherein the first end of the filament is attached to the chamber and the second end is attachable to at least one electrochemical cell housed in the chamber to thereby hang the cell in the vacuum by the filament; and
    c) at least one heat energy measuring device disposed within the chamber to measure heat energy emitted from the cell.

13. The system of claim 12 wherein the electrochemical cell is suitable for implantable medical applications.

14. The system of claim 12 wherein the chamber can accommodate a plurality of electrochemical cells and the at least one heat energy measuring device is arranged to individually measure the plurality of electrochemical cells.

15. The system of claim 14 wherein each electrochemical cell is associated with a separate heat energy measuring device.

16. The system of claim 12 wherein the chamber is configured to reduce the pressure therein to a range of 0 to about 0.001 Torr.

17. The system of claim 12 wherein the at least one heat energy measuring device is configured to measure heat energy in the range of 0 to 100 microwatts.

18. The system of claim 12 wherein the at least one heat energy measuring device is a thermocouple.

19. The system of claim 12 wherein the at least one heat energy measuring device is a non-contact infrared sensing device.

20. The system of claim 19 wherein the non-contact infrared sensing device is moveable within the chamber during measurement operations.

21. The system of claim 12 wherein the filament is a fine wire or thread of relatively low thermal conductivity and a relatively high ratio of length to cross-sectional area.

22. The system of claim 12 wherein the filament is selected from the group consisting of glass, ceramics, and thermoplastic materials.

23. The system of claim 12 wherein the filament is of a spun or foamed construction.

24. A system for testing electrochemical cells for defects, comprising:
   a) a chamber configured to accommodate a plurality of electrochemical cells in a reduced pressure environment;
   b) a plurality of filaments each having a length between a first end attached to the chamber and a second end attached to respective ones of the electrochemical cells to thereby hang the cells in the chamber in the reduced pressure environment; and
   c) a plurality of heat energy measuring devices disposed within the chamber and arranged to individually measure heat energy emitted from respective ones of the plurality of electrochemical cells.

25. A system for testing electrochemical cells for defects, comprising:
   a) a chamber configured for having a reduced pressure environment therein;
   b) a plurality of filaments each having a length between a first end attached to the chamber and a second end attached to respective ones of the electrochemical cells to thereby hang the cells in the chamber in the reduced pressure environment; and
   c) at least one heat energy measuring device disposed within the chamber and configured to measure heat energy emitted from the respective cells in the range of 0 to 100 microwatts.

26. A system for testing electrochemical cells for defects, comprising:
   a) a chamber configured for having a reduced pressure environment therein;
   b) a plurality of filaments each having a length between a first end attached to the chamber and a second end attached to respective ones of the electrochemical cells to thereby hang the cells in the chamber in the reduced pressure environment; and
   c) at least one non-contact infrared heat energy sensing device movable within the chamber for measuring heat energy emitted from respective ones of the cells.

* * * * *

UNITED STATES PATENT AND TRADEMARK OFFICE
CERTIFICATE OF CORRECTION

| | | |
|---|---|---|
| PATENT NO. | : 7,230,430 B1 | Page 1 of 1 |
| APPLICATION NO. | : 11/164548 | |
| DATED | : June 12, 2007 | |
| INVENTOR(S) | : Donald F. Kaiser | |

It is certified that error appears in the above-identified patent and that said Letters Patent is hereby corrected as shown below:

Column 5, line 12, delete "100" and insert --110--.

Signed and Sealed this

First Day of July, 2008

JON W. DUDAS
*Director of the United States Patent and Trademark Office*